(12) United States Patent
Gustafson et al.

(10) Patent No.: US 10,688,273 B2
(45) Date of Patent: Jun. 23, 2020

(54) DUAL PRESSURE RESPIRATORY ASSISTANCE DEVICE

(71) Applicant: The Board of Trustees of Western Michigan University, Kalamazoo, MI (US)

(72) Inventors: Peter Allen Gustafson, Schoolcraft, MI (US); Joseph David Hudson Taylor Barnett, Lawton, MI (US); Stephen Chiramukathu John, Ann Arbor, MI (US); Hoa Tri Le, Kentwood, MI (US)

(73) Assignee: The Board of Trustees of Western Michigan University, Kalamazoo, MI (US)

(*) Notice: Subject to any disclaimer, the term of this patent is extended or adjusted under 35 U.S.C. 154(b) by 321 days.

(21) Appl. No.: 15/650,443

(22) Filed: Jul. 14, 2017

(65) Prior Publication Data
US 2017/0312475 A1 Nov. 2, 2017

Related U.S. Application Data

(63) Continuation-in-part of application No. PCT/US2016/013606, filed on Jan. 15, 2016.
(Continued)

(51) Int. Cl.
*A61M 16/20* (2006.01)
*A61M 16/06* (2006.01)
(Continued)

(52) U.S. Cl.
CPC ........ *A61M 16/209* (2014.02); *A61M 16/201* (2014.02); *A61M 16/0006* (2014.02);
(Continued)

(58) Field of Classification Search
None
See application file for complete search history.

(56) References Cited

U.S. PATENT DOCUMENTS

| | | | |
|---|---|---|---|
| 2005/0072470 | A1 | 4/2005 | Jacobs et al. |
| 2008/0149099 | A1 | 6/2008 | Doyle |

(Continued)

FOREIGN PATENT DOCUMENTS

| | | | |
|---|---|---|---|
| CN | 102438571 A | 5/2012 | |
| CN | 202822380 U | 3/2013 | |

(Continued)

OTHER PUBLICATIONS

International Search Report, Application No. PCT/US2016/013606, dated May 12, 2016, 8 pages.

*Primary Examiner* — Kendra D Carter
*Assistant Examiner* — Suraj Kandalam
(74) *Attorney, Agent, or Firm* — Price Heneveld LLP

(57) ABSTRACT

A dual pressure respiratory assistance device including a gas source which supplies a flow of gas into an air tube having a bubbler branch and a patient branch. A first tube that is connected to the bubbler branch is at least partially submerged in a fluid. An oscillatory relief valve cycles between first and second configurations. The relief valve includes an oscillating member which captures gas released through at least one hole in the first tube when the oscillating member is in a first position. The gas in the oscillating member causes the oscillating member to rise to a second position, wherein gas is released from the oscillating member and the at least one hole is blocked when the oscillating member reaches the second position.

20 Claims, 12 Drawing Sheets
(3 of 12 Drawing Sheet(s) Filed in Color)

Related U.S. Application Data

(60) Provisional application No. 62/104,233, filed on Jan. 16, 2015.

(51) Int. Cl.
  *A61M 16/08* (2006.01)
  *A61M 16/00* (2006.01)
  *A61M 16/16* (2006.01)

(52) U.S. Cl.
  CPC ....... *A61M 16/0096* (2013.01); *A61M 16/024* (2017.08); *A61M 16/0666* (2013.01); *A61M 16/0875* (2013.01); *A61M 16/16* (2013.01); *A61M 16/208* (2013.01); *A61M 2016/003* (2013.01); *A61M 2202/0208* (2013.01); *A61M 2205/3348* (2013.01); *A61M 2240/00* (2013.01)

(56) References Cited

U.S. PATENT DOCUMENTS

| | | |
|---|---|---|
| 2011/0079222 A1* | 4/2011 | DiBlasi ............... A61M 16/021 128/203.12 |
| 2012/0024286 A1 | 2/2012 | Boring |
| 2012/0160242 A1* | 6/2012 | Gutierrez Fonseca ..................... A61M 16/021 128/203.26 |
| 2012/0204970 A1 | 8/2012 | McAuley et al. |
| 2012/0285454 A1 | 11/2012 | Nibu et al. |
| 2013/0269693 A1 | 10/2013 | Neatrour et al. |
| 2014/0166013 A1 | 6/2014 | Stenzler et al. |
| 2017/0095628 A1* | 4/2017 | Bartlett, II ........ A61M 16/0463 |

FOREIGN PATENT DOCUMENTS

| | | |
|---|---|---|
| WO | 2006004439 A2 | 1/2006 |
| WO | 2012020387 A1 | 2/2012 |
| WO | 2014026227 A1 | 2/2014 |

\* cited by examiner

DUAL PRESSURE RESPIRATORY ASSISTANCE DEVICE

CROSS-REFERENCE TO RELATED APPLICATIONS

This application is a Continuation-in-Part of International Application No. PCT/US2016/013606, filed Jan. 15, 2016, entitled "DUAL PRESSURE RESPIRATORY ASSISTANCE DEVICE," which claims the benefit of U.S. Provisional Application No. 62/104,233, filed on Jan. 16, 2015, entitled "DUAL PRESSURE RESPIRATORY ASSISTANCE DEVICE," the entire contents of each of which are incorporated herein by reference.

FIELD OF THE INVENTION

The present disclosure relates to a dual pressure respiratory assistance device, a method of treating patients using the same, and a kit for converting a bubble continuous positive airway pressure (bubble-CPAP) device to a dual pressure respiratory assistance device.

BACKGROUND

Bubble Continuous Positive Airway Pressure (bubble-CPAP) is a widely used respiratory technology for premature neonates around the world. It is simple, effective and especially applicable in rural areas. Bubble-CPAP devices include a water column with a tube submerged in the water column, where the depth of the submerged tube indicates the backpressure delivered by the device. Physically, the tube is submerged in the water column, and air bubbles escape out of the bottom of the tube. Thus, within the tube and all associated piping of the bubble-CPAP, a backpressure directly proportional to the submerged depth of the tube is maintained. The Continuous Positive Airway Pressure (CPAP) recruits and stabilizes the infant's alveoli in their lungs. Results obtained using bubble-CPAP are comparable to results obtained using traditional ventilator CPAP. However, for infants suffering moderate to severe respiratory distress, CPAP (either ventilator or bubble) is inadequate. Variable level or Dual Positive Airway Pressure (Bi-PAP or NIPPV), consisting of a cyclic oscillation between the lower pressure (Positive End Expiratory Pressure or PEEP) and a higher pressure (Peak Inspiratory Pressure or PIP) may be utilized to recruit and stabilize the alveoli in infants with severe respiratory distress if CPAP is insufficient. This may be done with a conventional mechanical ventilator or other technology. However, due to the expense and complexity, it is not always possible to offer ventilator access to patients. Therefore, in the absence of mechanical ventilators or similar technologies, many patients with moderate to severe respiratory distress are not adequately treated.

BiPAP and Non-Invasive Positive Pressure Ventilation (NIPPV), the next levels of clinical respiratory treatment utilized to assist premature babies in breathing, involves a cyclic oscillation between the baseline pressure and a higher level. For example, typical BiPAP pressures may include oscillation between 8 cm and 5 cm of water pressure at a frequency of about 0.66 Hz, while NIPPV pressures may include oscillation between about 20 cm and 5 cm of water pressure at the same frequency. However, BiPAP and NIPPV are typically only available in more developed countries, using conventional mechanical ventilators or BiPAP machines. These devices are expensive, require additional continuous supply of electricity and are difficult to maintain and service. In some regions, large sectors of the population may not have access to ventilators or BiPAP machines. In the context of respiratory care, invasive treatment typically refers to the placement of a tube in the patient's trachea to assist with ventilation ("intubation"). Recently there has been increased interest in non-invasive forms of treatment, like bubble CPAP, to reduce damage to infant trachea and lungs. This is also particularly relevant for settings which may not have facilities for intubation. BiPAP or NIPPV is typically delivered as a noninvasive treatment in contrast to mechanical ventilation and can reduce hospital stay in comparison to standard CPAP or bubble-CPAP. In BiPAP or NIPPV devices, an oscillating pressure functions to recruit and stabilize alveoli, the functional units of the lungs. The modulating pressures produced by the BiPAP or NIPPV function are theorized to assist breathing and to remind the patient to breathe, facilitating a more rapid recovery.

In addition to use with neonates, BiPAP and NIPPV ventilation can be useful in treating patients of all ages, and can be used to provide respiratory assistance to patients with many different conditions. BiPAP and NIPPV are known treatments for many respiratory conditions, such as those arising from Congestive Heart Failure, Chronic Obstructive Pulmonary Disease and Asthma and are known to be useful for respiratory support during surgical procedures. These treatments are also commonly used in patients with sleep apnea.

SUMMARY

One aspect of the present disclosure is a variable (e.g. dual) pressure respiratory assistance device including a gas source which supplies a flow of gas into a passageway such as an air tube. The air tube has a bubbler branch and a patient branch. A first tube disposed at the terminal end of the bubbler branch is at least partially submerged in a fluid. An oscillatory relief valve is disposed on the first tube. The oscillatory relief valve includes an oscillating member such as an inverted basket which captures gas bubbles released through at least one hole in the first tube when the inverted basket is in a first position. The collection of gas in the inverted basket alters the buoyancy and thus causes the basket to rise through the fluid to a second position, covering at least one hole on the central tube and forcing as bubbles to escape from the end of the tube. Gas is released from the inverted basket when the inverted basket reaches the second position, whereby the oscillatory relief assembly causes the pressure in the patient branch to cycle between a first pressure range and a second pressure range. As pressure is set by the depth at which bubbles escape the central tubing, in the first position the pressure in the patient branch is lower, as bubbles escape through at least one hole in the central tube (set higher in the tubing). In the second position, the pressure is higher, as bubbles escape from the end of the central tube (set lower on the tubing).

Another aspect of the present disclosure is a dual pressure respiratory assistance device including an oscillatory relief valve positionable in a first baseline pressure position on an at least partially submerged first tube and a second peak pressure position on the first tube. The oscillatory relief valve is powered to cycle between the first baseline pressure position and the second peak pressure position using air flow and gravity.

Another aspect of the present disclosure is a kit for converting a bubble-CPAP machine to a dual pressure respiratory assistance device, including a cylindrical shell and an inverted basket attachment. The cylindrical shell has a circumferential side wall having at least one window therethrough. The cylindrical shell is sized to fit around a first tube which is at least partially submerged in a fluid. The inverted basket attachment has a top portion which fits closely around the side wall of the cylindrical shell and is able to slide with respect to the cylindrical shell. An upper wall extends from the top portion to capture gas bubbles therein and thereby adjust the buoyancy of the inverted basket attachment.

Yet another aspect of the present disclosure is a method of providing respiratory assistance to a patient, including the steps of initiating a gas flow into an air passageway such as a tube. The passageway may branch at one point into at least a bubbler branch and a patient branch. The passageway may branch into a second patient branch and/or other branches. The bubbler branch with an oscillatory relief valve disposed thereon is at least partially submerged in a container of fluid. Positioning a patient air supply interface on a patient for use, wherein the patient air supply interface is fluidly connected to the patient branch.

These and other features, advantages, and objects of the present device will be further understood and appreciated by those skilled in the art upon studying the following specification, claims, and appended drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 2:
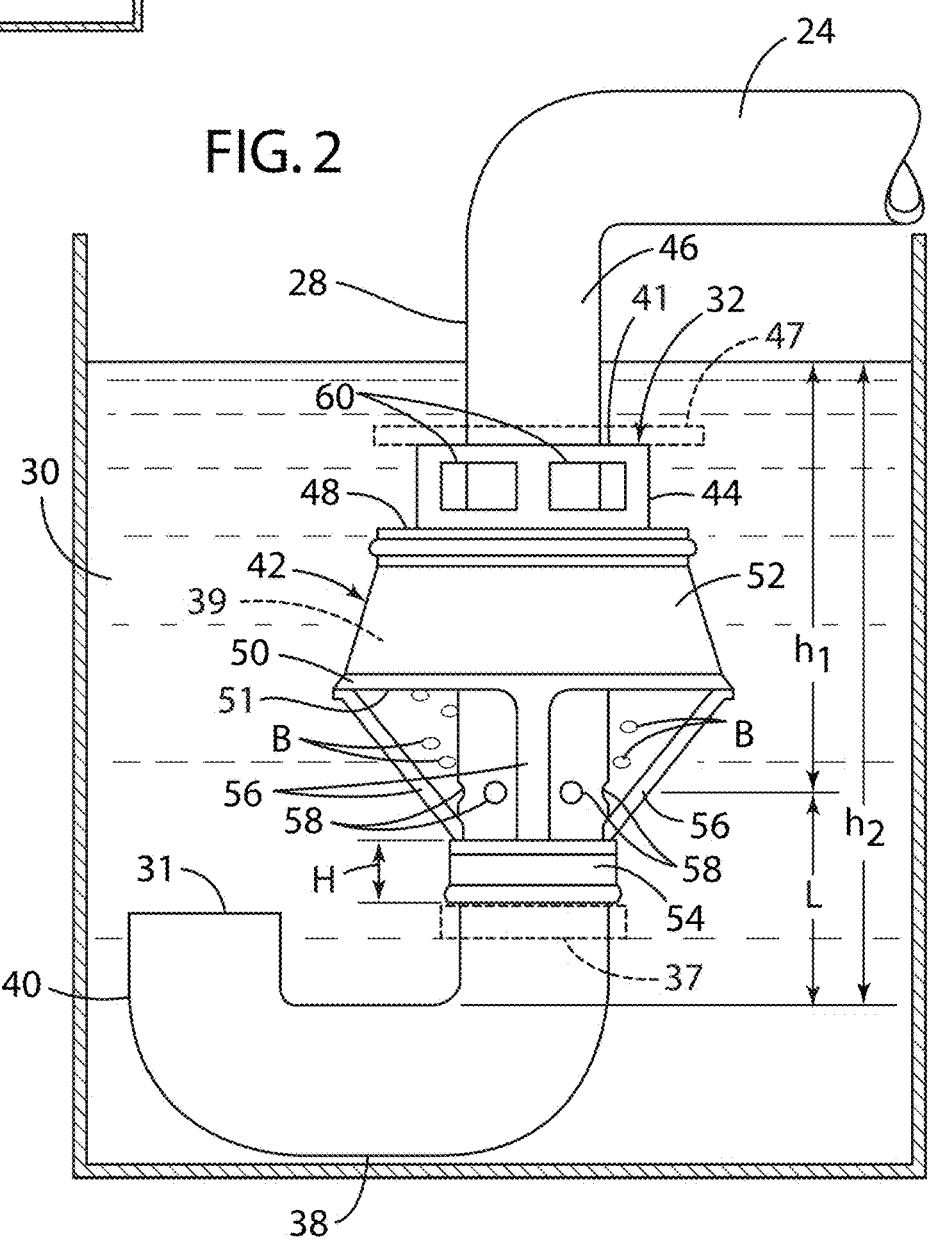
FIG. 2 is a side elevational view of one embodiment of a vertical submerged tube with an oscillatory relief valve mechanism for a dual pressure respiratory device in a first or Positive End Expiratory Pressure (PEEP) pressure position.

For purposes of description herein the terms "upper," "lower," "right," "left," "rear," "front," "vertical," "horizontal," and derivatives thereof shall relate to the variable/dual pressure respiratory assistance device and its components as shown in the side elevation view as shown in FIG. 2. However, it is to be understood that the dual pressure respiratory assistance device and its components may assume various alternative orientations and the methods for creating non-constant air pressure may include various step sequences, except where expressly specified to the contrary. It is also to be understood that the specific compositions, devices and processes illustrated in the attached drawings, and described in the following specification are simply exemplary embodiments of the inventive concepts defined in the appended claims. Hence, specific compositions, dimensions and other physical characteristics relating to the embodiments disclosed herein are not to be considered as limiting, unless the claims expressly state otherwise.

Figure 1:
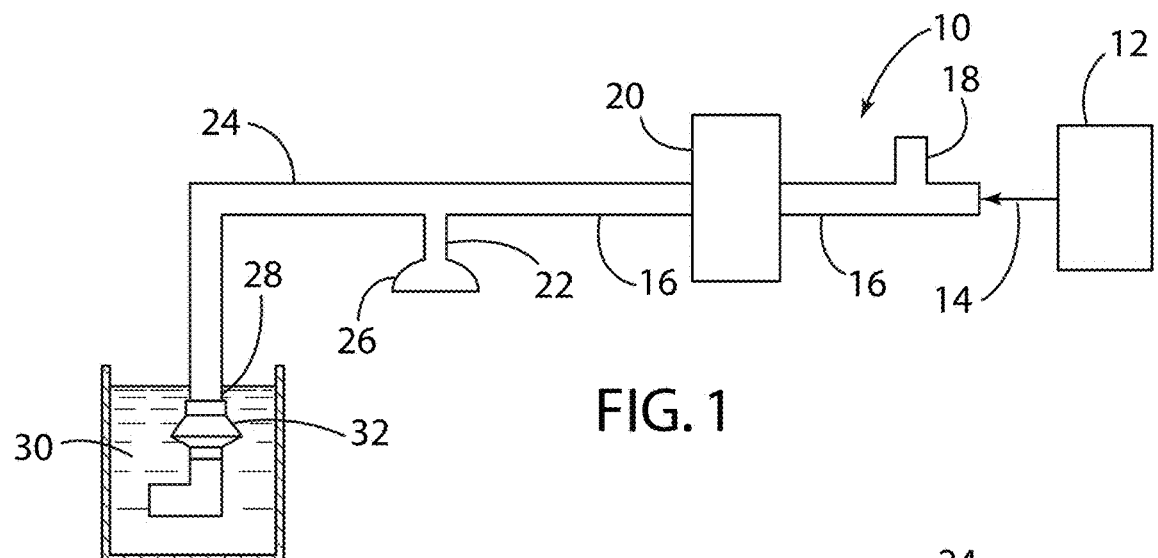
FIG. 1 is a schematic of a dual pressure respiratory assistance device.
Figure 5:
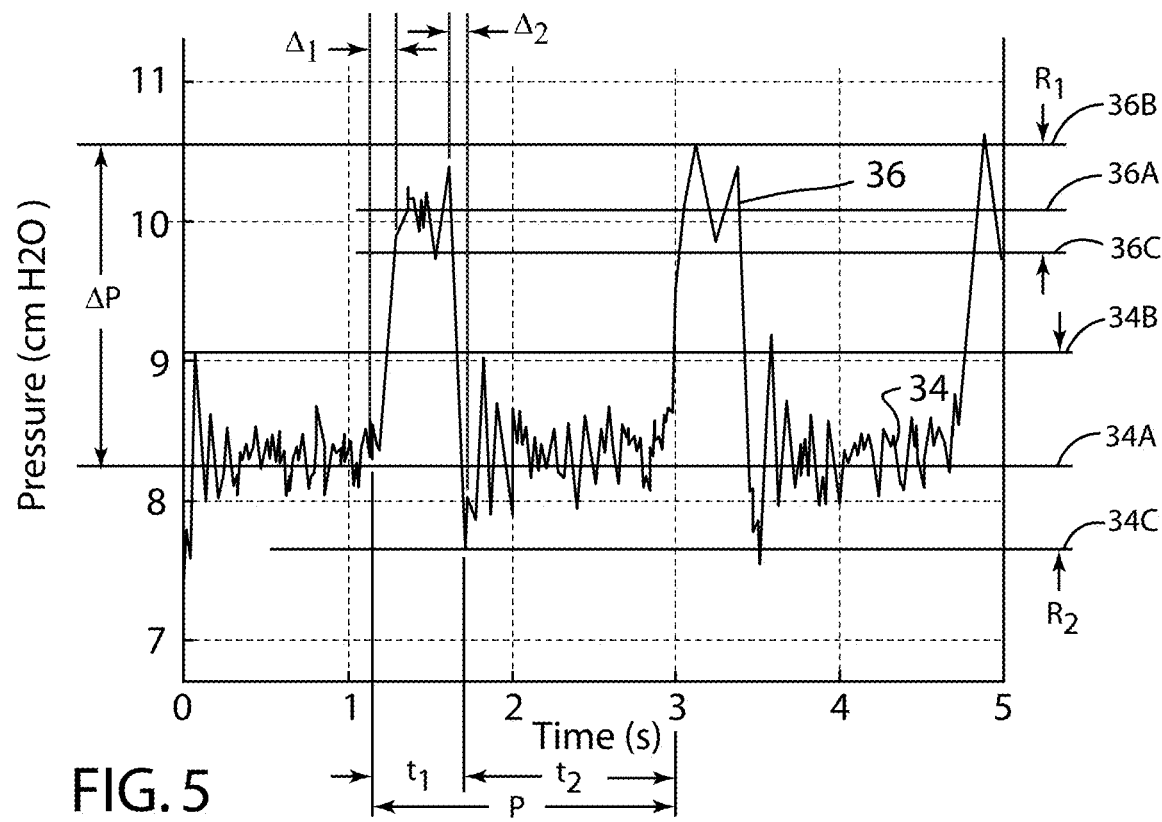
FIG. 5 is a graph illustrating the amplitude of the air back pressure over time for an embodiment of a dual pressure respiratory assistance device.

As shown in the embodiment depicted in FIG. 1, a dual pressure respiratory device 10 includes a gas source 12 which supplies a flow of gas 14 into a passageway such as air tube 16. The flow of gas 14 into the air tube 16 can be monitored and controlled using a flowmeter 18 and/or a needle valve 62 (FIG. 7), and the humidity controlled using a humidifier 20 or dehumidifier device between the gas source 12 and the patient. The system may also include an electrical heating element (not shown) to facilitate heating and/or vaporization of the water. The flow of gas 14 from gas source 12 may be at a constant mass/volume and a constant pressure. The air tube 16 splits into a patient branch 22 and a bubbler branch 24. The patient branch terminates in a patient air supply interface 26, including without limitation air supply interfaces such as nasal cannula, a mask, or other known patient air supply interfaces 26. The bubbler branch 24 terminates with a first passageway which may be formed by a first tube 28 at least partially submerged in a fluid 30. In certain preferred embodiments, the first tube 28 is generally vertically oriented, and is also referred to herein as the "vertical tube" 28. The first tube 28 has an oscillatory relief valve mechanism 32 fitted thereon. The oscillatory relief valve mechanism 32 enables the supply of air to a patient which cycles between a baseline pressure 34 and a peak pressure 36 (as shown in FIG. 5), resulting in oscillating dual pressure air supply to the patient. The pressure may be maintained at relatively constant base and peak pressure levels 34 and 36, respectively, for required periods of time, and the pressure may change or transition between the base and peak levels 34 and 36, respectively. The transition time may vary as required for a particular application. As discussed below, the configuration of the oscillatory relief valve mechanism 32 may be adjusted/varied to adjust the magnitude of the base and peak pressure levels 34 and 36, and the lengths of time that the base and peak pressure levels 34 and 36 are maintained.

The oscillatory relief valve mechanism 32, as further described herein, allows the oscillating dual pressure air supply to be maintained through a single power source, the gas source 12, and can be used to retrofit an existing bubble-CPAP device into the dual pressure respiratory device 10 described herein. The oscillating pressure of the dual pressure respiratory assistance device 10 functions to recruit and stabilize the functional units of the lungs, the alveoli. The modulating pressures are theorized to assist the patient's breathing, as well as reminding the patient to breathe, facilitating a more rapid recovery.

Figure 7:
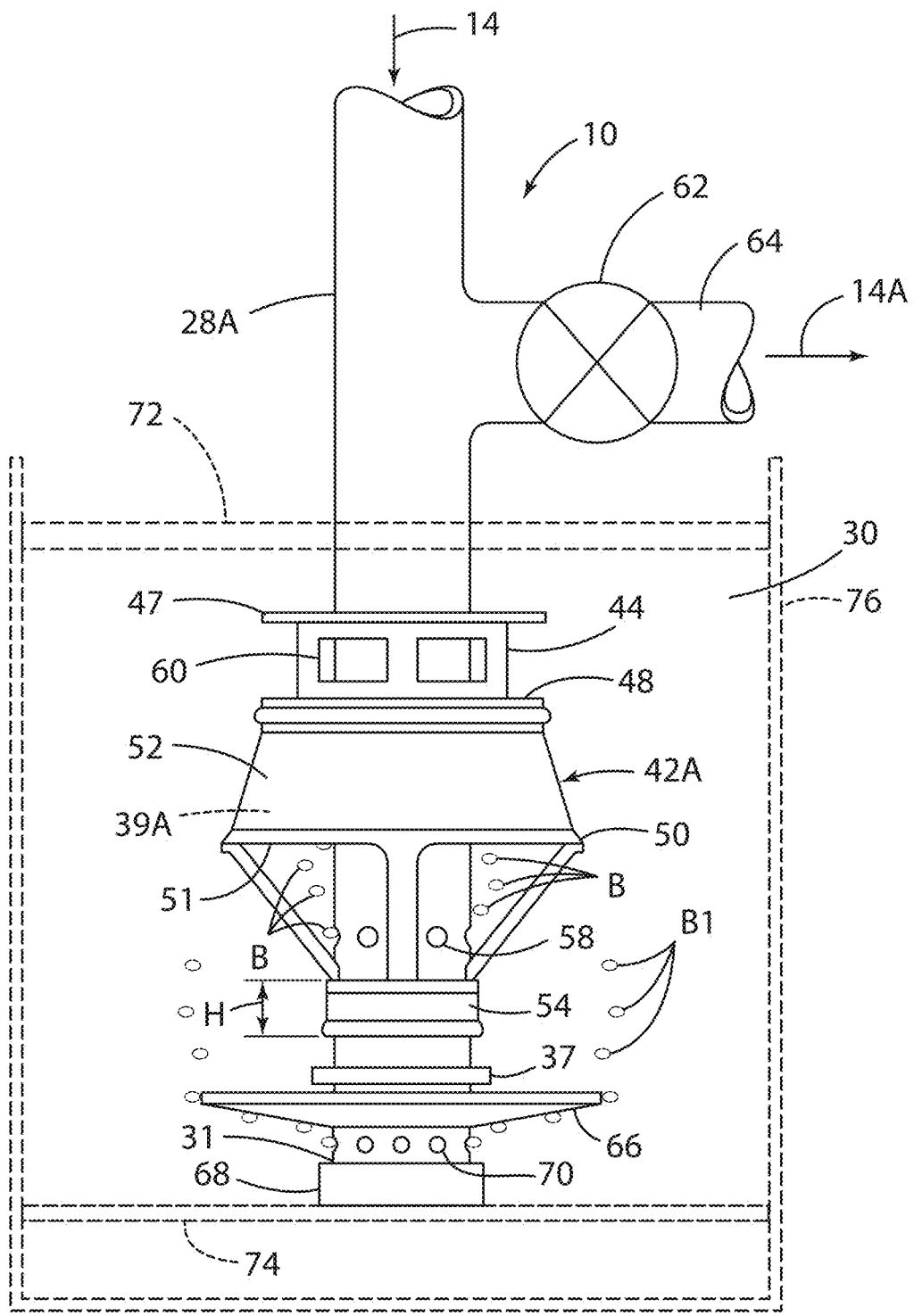
FIG. 7 is a side elevational view of another embodiment of an oscillatory relief valve mechanism.

As shown in more detail in the embodiment depicted in FIG. 2, the bubbler branch 24 of the air tube 16 terminates in the first tube 28, and optionally a hydrodynamically tuned horizontal or nearly horizontal tube 38 and a vertical return tube 40. In certain embodiments, the bubbler branch 24 of the air tube 16 terminates in only a first tube 28; or a first tube 28 and a horizontal tube 38. The air escapes through an outlet 31, which can be provided at the end of the first tube 28, or at the end of the optional horizontal tube 38 or vertical return tube 40, as applicable. In one set of preferred embodiments, the first tube 28 is generally vertically oriented. In alternate embodiments, the first tube 28 could be disposed or positioned at an angle or have a portion which is positioned at an angle, although a generally vertical configuration minimizes friction effects for the oscillatory relief valve mechanism 32 to travel between the baseline pressure 34 position and the peak pressure 36 position. The effective depth that the first tube 28 is submerged in the fluid 30 limits the higher pressure of the gas in the peak pressure mode. The effective depth of the first tube 28 is the vertical distance from the surface of the fluid 30 to the lowest point that the air must descend under the top surface of the fluid 30 before traveling back in an upward direction. The waveform or timing of the transition between the PEEP (baseline) pressure 34 and the PIP (peak) pressure 36 of the gas supplied to the patient is regulated through the oscillatory relief valve mechanism 32 and a "leak valve" such as needle valve 62 (FIG. 7).

Figure 3:
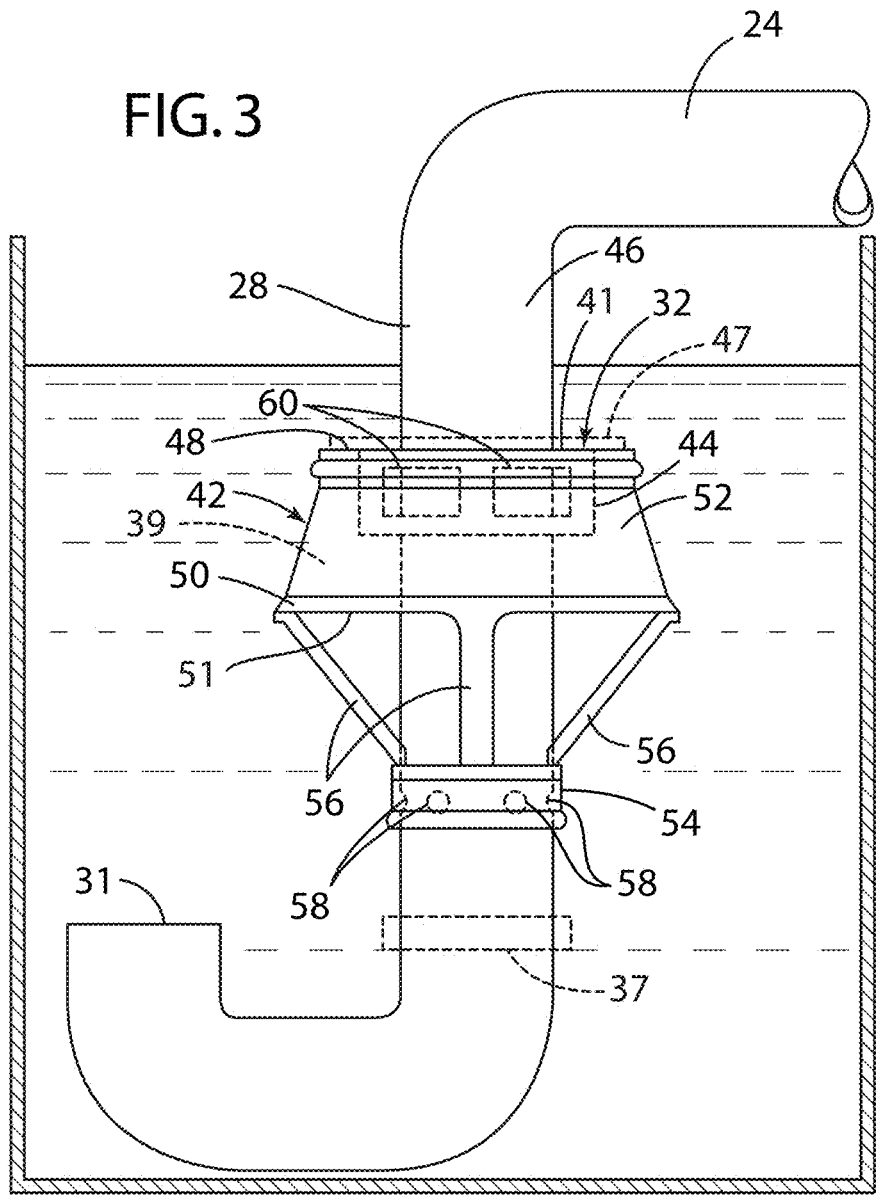
FIG. 3 is a side elevational view of the vertical submerged tube with the oscillatory relief valve mechanism for the dual pressure respiratory device of FIG. 2 in a second peak position.
Figure 4:
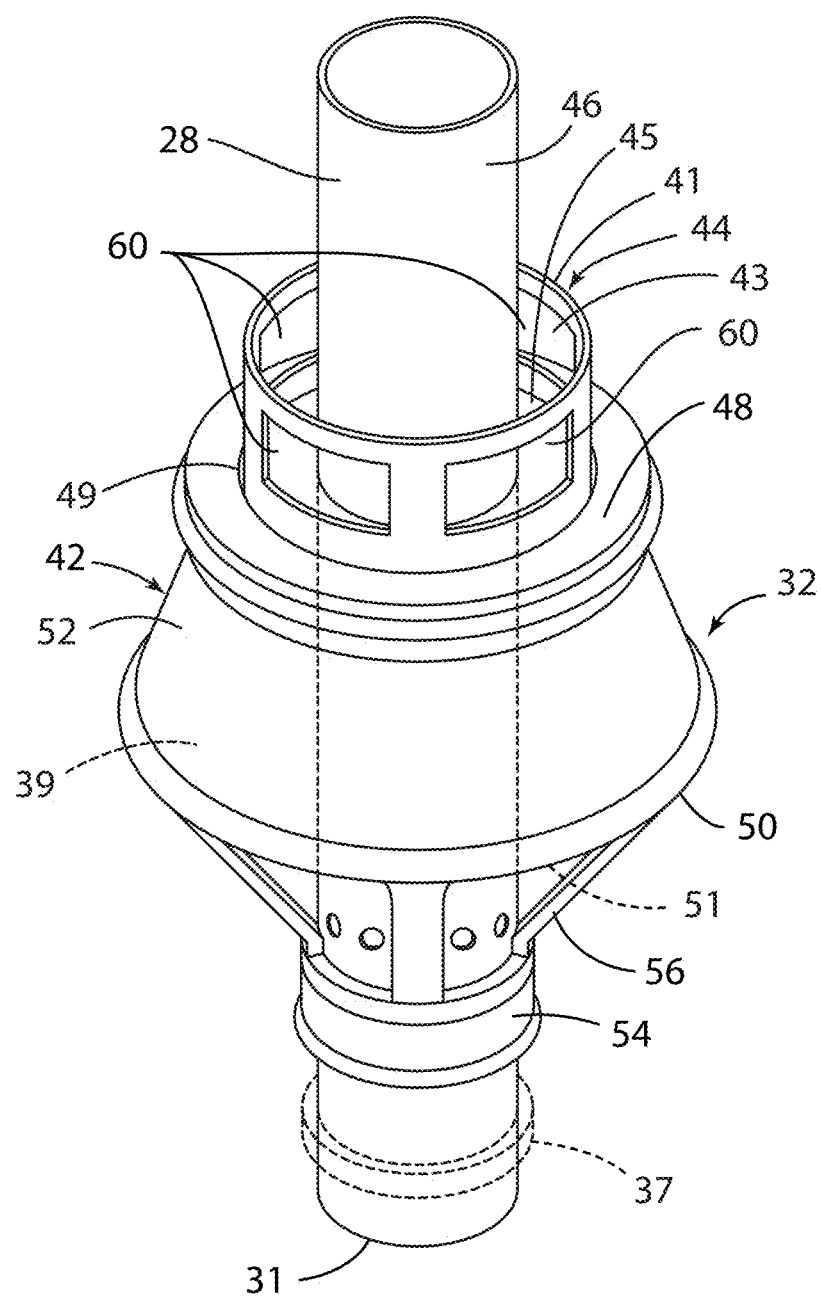
FIG. 4 is a top perspective view of the vertical submerged tube with the oscillatory relief valve mechanism for the dual pressure respiratory device of FIG. 2 in the first baseline pressure position.

In greater detail, as shown in the embodiments depicted in FIGS. 2-4, the oscillatory relief valve mechanism 32 includes an oscillating member such as an inverted basket 42 which fits around a cylindrical shell 44. As discussed below, basket 42 is slidably disposed on cylindrical shell 44. During operation, basket 42 shifts vertically relative to cylindrical shell 44 in an oscillating manner. The cylindrical shell 44 is affixed about the central shaft 46 of the submerged first tube 28 by an annular sidewall 45 (FIG. 4). The inverted basket 42 includes an annular top wall 48 having a circular opening 49 (FIG. 4) which closely but slidably fits around the cylindrical shell 44. Basket 42 also includes a bottom circumference 50 having a diameter which may be equal to or greater than the diameter of top wall 48. The diameter of circumference 50 may also be less than the diameter of top wall 48. In the embodiment depicted in FIGS. 2-4, a generally solid conical wall 52 connects the top wall 48 to the bottom circumference 50 to form the inverted basket 42 and to define an internal space 39 that opens downwardly via downwardly facing opening 51. The basket 42 is also mechanically attached to a sleeve 54 using supports 56. The sleeve 54 is suspended below the inverted basket 42, and fits closely around the first tube 28. When basket 42 is in a first position, as illustrated in FIG. 2, a plurality of circumferential holes 58 in submerged first tube 28 are provided around the circumference of the submerged first tube 28 between the inverted basket 42 and the sleeve 54.

In operation, when the basket 42 is in the first (lower) position (FIG. 2), bubbles B from the gas supply 12 escape through the circumferential holes 58 between the sleeve 54 and the basket 42. The bubbles B travel up the exterior of the first tube 28 through opening 51 into internal space 39 of inverted basket 42. The gas/bubbles B are trapped in internal space 39 under the walls 48 and 52 of the inverted basket 42. When enough gas from bubbles B accumulates in internal space 39 of basket 42, the resulting buoyant force causes the basket 42 and the attached sleeve 56 to rise within the fluid 30, gliding along the cylindrical shell 44 to an upper or second position in which sleeve 54 closes off holes 58 as shown in FIG. 3. The length/height "H" of sleeve 54 may be relatively small (e.g. 0.125 inches or 0.25 inches) or the length/height H may be greater (e.g. 0.5 inches, 1.0 inches, 3.0 inches, etc.) as required to provide proper operation of the device. For example, one or more ring-like sleeve segments (not shown) may be removably connected to sleeve 54 to increase or decrease the length/height of sleeve 54 as required. The depth $h_1$ of the circumferential holes 58 in the fluid 30 determines the baseline pressure 34 of the gas supplied to the patient, according to the hydrostatic pressure formula $P_1 = \gamma \times h_1$, where $P_1$ is the hydrostatic pressure, $\gamma$ (gamma) is a constant equal to the fluid density times the acceleration due to gravity, and $h_1$ is the submersion depth of the circumferential holes 58. Additionally, the size and shape of the solid wall 52 determines how much air the basket 42 is able to capture. The amount of air captured and the weight of the basket 42 and the weight of components attached to basket 42 determine how quickly the basket 42 rises to seal off the circumferential holes 58, affecting the frequency of operation of the dual pressure respiratory assistance device 10.

As shown in the embodiment depicted in FIG. 3, when the basket 42 rises to the second (upper) position due to the collection of gas bubbles B, the sleeve 54 surrounds and blocks the circumferential holes 58 in the vertical tube 28, preventing gas bubbles B from escaping therefrom. When the gas is not permitted to escape through the circumferential holes 58, it travels down to the end of the first tube 28 (or the end of the horizontal tube 38 or return vertical tube 40) to the outlet 31 (FIG. 4). The depth $h_2$ (FIG. 2) of the lowest point that the air must crest before moving back upwards in the first tube 28, horizontal tube 38, or vertical return tube 40 determines the peak pressure 36 of the gas supplied to the patient, according to the hydrostatic pressure formula $P_2 = \gamma \times h_2$, where $P_2$ is the hydrostatic pressure, $\gamma$ is a constant, and $h_2$ is the submersion depth of the lowest point that the air must descend under the fluid 30 before traveling back in an upward direction (i.e., at the bottom of the first tube 28 or the top wall of the horizontal tube 38, as applicable). In certain embodiments, depending on the relative dimensions of the tubing and the flow rate of the gas (including without limitation, where the gas flow rate is high with respect to the diameter of the tubing), alternate physical forces may be dominant. The peak pressure 36 can be proportional to the depth of the outlet 31, the lowest submersion depth, or any other depth where there is an air/fluid 30 interface along the tubing.

When the basket 42 is in the second (upper) peak position (FIG. 3), as the sleeve 54 covers the circumferential holes 58 in the first tube 28, the top wall 48 of the inverted basket 42 reaches a circumferential row of windows 60 (FIGS. 2-4) formed in the cylindrical shell 44. When the top wall 48 of the basket 42 moves above the windows 60 (FIG. 3), the accumulated air in internal space 39 of basket 42 which caused the basket 42 to rise is permitted to escape through the windows 60, and through an annular opening 43 (FIG. 4) formed between upper edge 41 of cylindrical shell 44 and the submerged first tube 28. When a sufficient amount of the air has escaped through the windows 60, the buoyancy of the inverted basket 42 decreases and basket 42 slides back down along the cylindrical shell 44 due to its weight, returning to the first (lower) position (FIG. 2) to initiate another cycle. An optional stop 37 (FIG. 2) in the form of a ring may be positioned on tube 28 to engage sleeve 54 and thereby limit the downward travel of basket 42. Similarly, an optional stop ring 47 (FIGS. 2 and 3) may be positioned adjacent upper edge 41 of cylindrical shell 44 to limit upward travel of basket 42. Stops 37 and/or 47 may be adjustably connected to tube 28 such that the vertical positions of stops 37 and/or 47 can be adjusted. Adjusting the number, size, shape, and orientation of the windows 60 can affect the rate at which air is released from under the basket 42, and the window 60 or windows 60 can be optimized to obtain a desired waveform for the dual pressure respiratory device 10.

Figure 6:
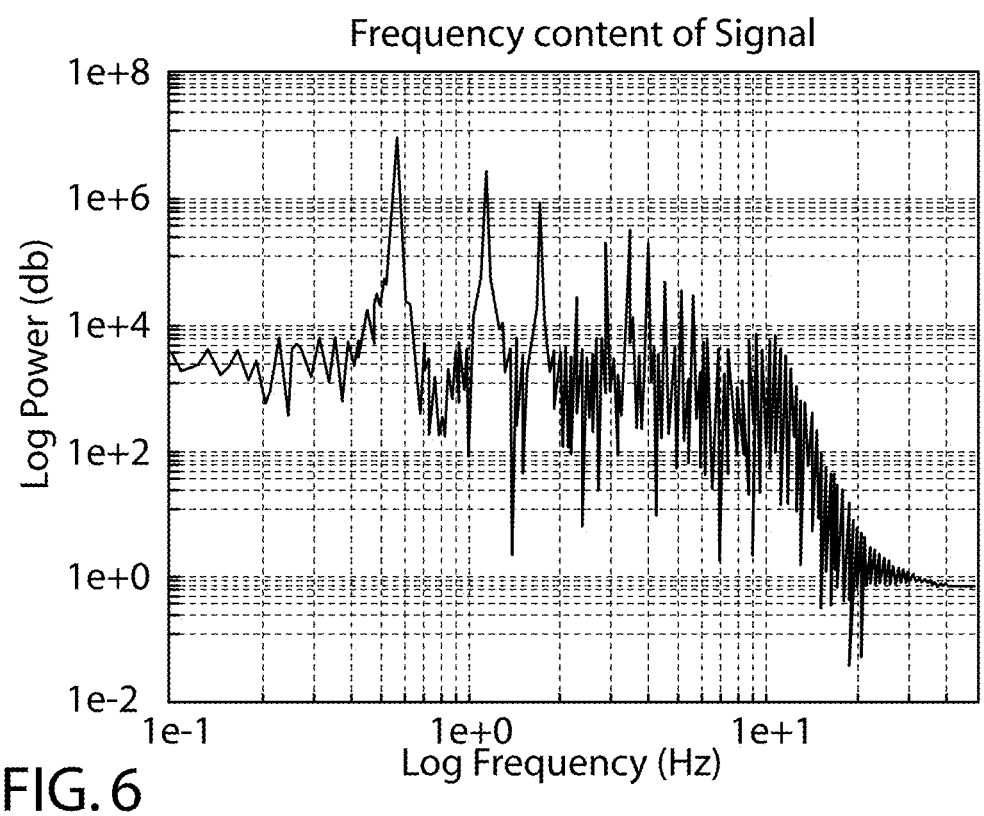
FIG. 6 is a graph illustrating the oscillation frequency content for one embodiment of an air driven dual pressure respiratory assistance device.

When the circumferential holes 58 are not covered, the effective length of the vertical tube 28 is X cm, where X is the depth of the circumferential holes 58 below the surface of the fluid 30. When the holes 58 are covered by the sleeve 54, the effective length of the tube 28 is X+L cm, where L is the distance between the circumferential holes 58 and the lowest point that the air must descend before traveling upward. Because hydrostatic pressure depends on the effective submerged depth that the air must travel, this change in the effective length through movement of the sleeve 54 results in a non-constant pressure waveform, as illustrated in FIG. 5. FIG. 6 illustrates the frequency content of the signal in the non-constant pressure waveform generated by one embodiment of the dual-pressure respiratory assistance device described herein.

By changing the depth that the vertical tube 28 is submerged in the fluid 30 the pressure of the air supplied to the patient can be changed, while maintaining the same change in amplitude of the pressure (e.g. from 8 cm $H_2O$/5 cm $H_2O$ to 10 cm $H_2O$/7 cm $H_2O$). By changing the effective length of the submerged vertical tube 28, such as through adding additional or longer tubing sections between the circumferential holes 58 and the maximum depth of the vertical tube 28, the amplitude of the pressure change can also be modified, allowing conversion between a BiPAP-like functionality and a NIPPV-like functionality (e.g., changing from 8 cm $H_2O$/5 cm $H_2O$ to 20 cm $H_2O$/5 cm $H_2O$). Tubes of different lengths can be readily connected between the circumferential holes 58 and the lowest point that the air travels in the tubing. Increasing or decreasing the length of the tube 28 below holes 58 permits adjustment of the length of time $t_1$ (FIG. 5) at increased pressure, thereby allowing users to vary the pressure differential of the dual pressure respiratory assistance device 10 as required for a particular application/patient.

With low flow rates, a single first tube 28 can be used. The horizontal tube 38 is allows a bi-level waveform when higher flow rates are provided. Horizontal tube 38 also directs bubbles exiting outlet 31 away from inverted basket 42 such that bubbles exiting outlet 31 do not enter basket 42. By increasing the weight of the basket 42, the minimum flow rate at which the horizontal tube 38 is needed to modulate the bi-level waveform can be increased. At typical flow rates, as the flow rate is increased, the difference between the peak pressure 36 mean and the baseline pressure 34 mean can be increased, to the limiting pressure difference specified by the distance L (FIG. 2) between the circumferential holes 58 and the lowest point that the air must descend in the tube 28, 38, 40 before moving back upwards. At atypical flow rates, back pressure can be dominated by frictional losses. Additionally, increasing the flow rate alters the percentage of time that the dual pressure respiratory assistance device 10 operates at the peak pressure 36, which can be increased from below 10% to above 90%. The ready, simple adjustment of the baseline pressure 34, the peak pressure 36, the frequency of oscillation, and the percentage of time at each level 34, 36 allows optimization of the device 10 for patient care, and allows customization of the device 10 for a particular patient or particular use by using simple mechanical adjustment such as adding lengths of tubing or adding weight to the basket 42 or adjusting flow rate.

In one preferred embodiment, the dual pressure respiratory assistance device 10 has a frequency of 10 to 45 cycles per minute. In such an embodiment, the amplitude and the pressure range can be adjusted through the use of different lengths of pipe for the first tube 28 or various levels of fluid 30 for submerging the first tube 28.

The inverted basket 42 and sleeve 54 for use herein can be manufactured in two or more portions, and fitted together around the cylindrical shell 44. Pins or tabs can be provided to aid in alignment of the portions of the inverted basket 42, and silicon O-rings can optionally be used to seal the portions of the inverted basket 42. In alternate embodiments, the inverted basket 42 can be formed from a single piece that can be slid along the length of the first tube 28 to position the basket 42. The tolerance between the cylindrical shell 44 and the inverted basket 42 is sized to reduce friction between the opening 49 in top wall 48 and the cylindrical shell 44, while still preventing air leakage between the top wall 48 and the cylindrical shell 44 until the basket 42 has risen to the level of the windows 60 in the cylindrical shell 44. The tolerance is determined with reference to the surface tension of the fluid 30. Therefore, the surface tension of the fluid 30 can be adjusted through addition of surface acting agents or use of different fluids 30 to optimize the operation of the basket 42 around the cylindrical shell 44.

In certain preferred embodiments, kits can be prepared to convert a bubble-CPAP device to a dual pressure respiratory assistance device 10 as described herein. Such a kit can include the cylindrical shell 44, the inverted basket 42 with attached sleeve 54, and optionally a replacement first tube 28. Conversion kits can also include varying lengths of first tube 28 or vertical tube 28 attachments, as well as horizontal tube 38 and vertical return tube 40 portions. In other preferred embodiments, the first tube 28 of a traditional bubble-CPAP device can be altered by adding circumferential holes 58 therearound, and used with the cylindrical shell 44 and inverted basket 42 with attached sleeve 54.

To use the dual pressure respiratory assistance device 10 described herein, a gas flow 14 is initiated into the air tube 16 which branches into the bubbler branch 24 and the patient branch 22. The first tube 28 attached to the terminal end of the bubbler branch 24, having the oscillatory relief valve 32 disposed thereon, is at least partially submerged in a container of fluid 30. The patient air supply interface 26 attached to the terminal end of the patient branch 22 is positioned for use on the patient. The gas flow 14 through the air tube 16 actuates the oscillatory relief valve 32 as described herein, resulting in dual pressure supply of air to the patient, at a baseline pressure 34 and a peak pressure 36.

With further reference to FIG. 7, another version of the device 10 includes a tube 28A that receives gas 14, and a tube 64 that selectively routes a portion 14A of air 14 out of tube 28. A valve 62 controls the flow of air through the tube 64. Valve 62 may comprise a needle valve that may be adjusted to reduce pressure spikes/variations in the pressure levels 34 and 36 (FIG. 5). The needle valve 62 provides a precise metering of leaked air 14A to control the shape/form of the wave forms (pressure variation). The valve 62 may be adjusted to provide a required number of cycles per minute. A threaded cap 68 may be positioned on lower end 42 of tube 28A, and a plurality of openings 70 adjacent cap 42 form bubbles B1 during operation. A baffle 62 is secured to tube 28A above openings 70. Baffle 66 directs the bubbles B1 outwardly such that the bubbles B1 do not enter the basket 42. Horizontal tube 38 can act in place of a baffle 66. During operation, bubbles B from openings 58 enter basket 42 and provide for operation in substantially the same manner as discussed above in connection with FIGS. 1-6. Adjustable stops 37 and 47 may be utilized to control the range of vertical motion of basket 42 in operation. The vertical position of stops 37 and/or 47 may be vertically adjusted. Upper and/or lower braces 72 and 74, respectively, may be utilized to support and/or center the tube 28A in a cylindrical container 76. The container 76 may be filled with fluid such as water 30. The length/Height H of sleeve 54 may vary as discussed above in connection with FIG. 2. In one embodiment, brace 74 allows venting of air through the bottom of tube 28b. In another embodiment, lower brace 74 can cap tube 28b causing venting of air through holes 70 and 58.

Figure 8:
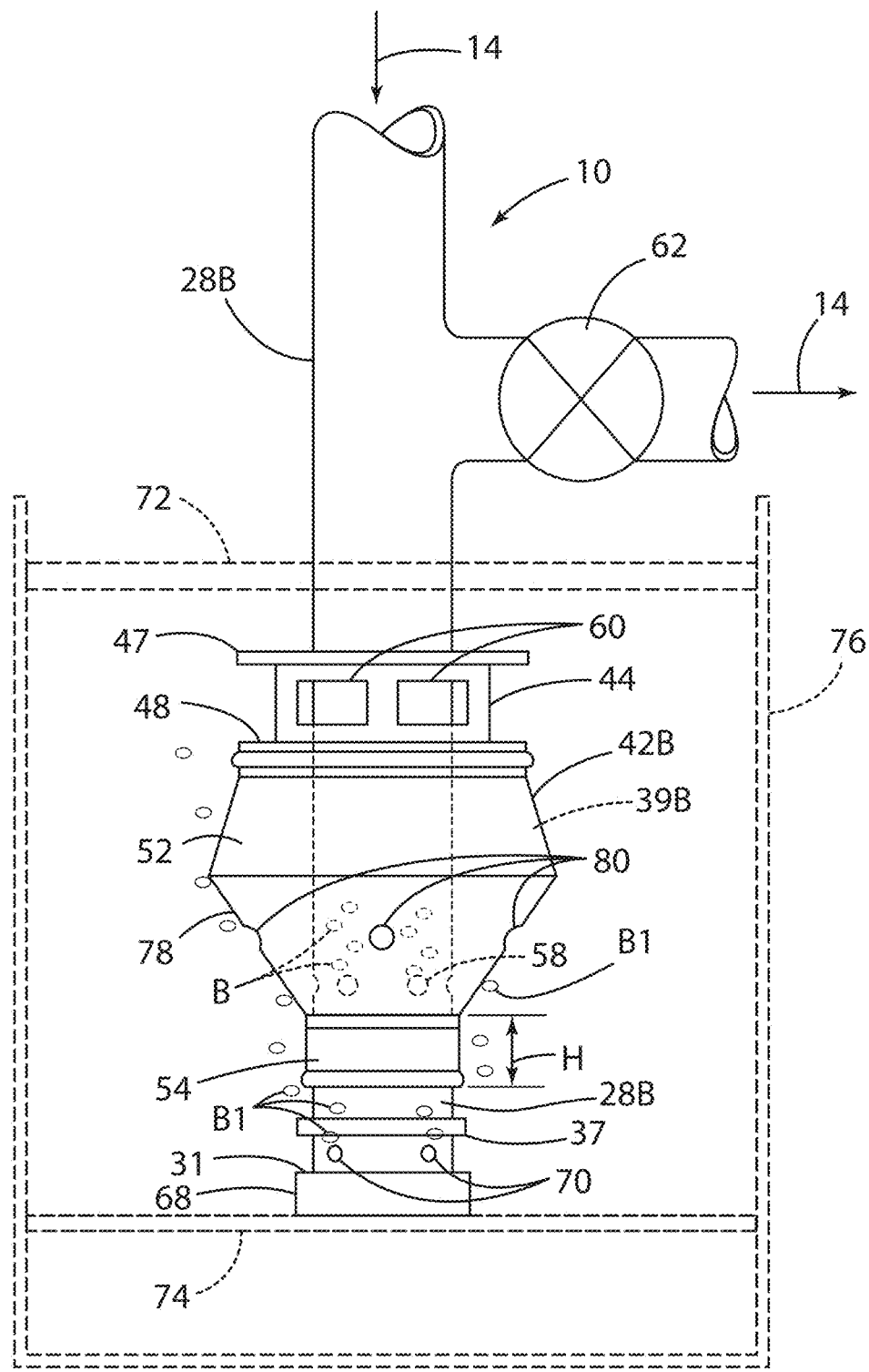
FIG. 8 is a side elevational view of another embodiment of an oscillatory relief valve mechanism.

With further reference to FIG. 8, a device 10 according to another aspect of the present disclosure includes a basket 42B having a generally conical lower wall 78 that extends between upper wall 52 and sleeve 54 to define an internal space 39B. When the basket 42B is in a lower position as shown in FIG. 8, openings 58 of tube 28B are disposed in internal space 39B of basket 42B, and bubbles B are formed by air exiting openings 58 in tube 28B. The bubbles B enter the internal space 39B and cause the basket 42B to rise as described in more detail above in connection with FIGS. 1-6. Tube 28B includes openings 70 adjacent a lower end 42 of tube 28B. Bubbles B1 from openings 70 do not enter internal space 39B of basket 42B due to the conical lower wall 78. Thus, the device of FIG. 8 utilizes a conical lower wall 78 of basket 42B to direct the bubbles B1 away from the internal space of basket 42B, rather than a baffle 66 as shown in the device of FIG. 7. The conical lower wall 78 may optionally include openings 80 (or other suitable fluid passageway) that allow flow of water in and out of the internal space 39B. Openings 80 may be positioned such that they are not directly above openings 70 such that bubbles B1 do not enter internal space 39B through openings 80. For example, openings 70 could be radially positioned at 0°, 90°, 180°, and 270° (in plan view) about a vertical center axis of tube 28B, and openings 80 could be located at 45°, 135°, 225° and 315°. The operation of the device of FIG. 8 is otherwise substantially the same as the version of FIG. 7. In particular, a needle valve 62 may be utilized to direct a selected portion 14A of gas 14 out of tube 28B to thereby control the frequency and/or other operating parameters of the device. The length/height H of sleeve 54 may vary as discussed above in connection with FIG. 2.

The oscillatory relief valve mechanisms described herein have a low cost of manufacture, are reliable, inexpensive to operate, and is dependent only on pressurized air for power, and not an additional electrical current. Thus, users who currently employ bubble-CPAP could use the presently disclosed dual pressure respiratory assistance device 10 without any additional power requirements. The device 10 is also optimized as an add-on for the widely used bubble-CPAP technology, which facilitates widespread use. The presently disclosed dual pressure respiratory assistance device 10 has several adjustable parameters, including: the baseline pressure 34 and peak pressure 36 (by adjusting the submerged depth of the first tube 28 and the distance between the circumferential holes 58 and the lowest point that the air must descend before turning upward); the percentage of time at the peak pressure 36 at a desired airflow rate (by adjusting the mass of the basket 42); the percentage of time at the peak pressure 36 (by adjusting the air flow rate and/or the length of the sleeve); etc. Additionally, because the device is optimized for bubble-CPAP set-ups, it also provides a hydro-oscillatory effect, the quasi-random variation of back pressure due to bubble release, which may provide an advantage to the lungs over traditional BiPAP or NIPPY.

Referring again to FIG. 5, peak pressure 36 may comprise an average or median peak pressure (line 36A), or the peak pressure 36 may comprise a first range of pressures $R_1$ which is equal to the distance between lines 36B and 36C, which represent the highest and lowest peak pressures, respectively. In the illustrated example, the highest peak pressure 36B is about 10.6 cm $H_2O$, and the lowest peak pressure 36C is about 9.7 cm $H_2O$. The median peak pressure 36A is about 10.2 cm $H_2O$, and the range $R_1$ (10.6-9.7) is about 0.9 cm $H_2O$. Similarly, baseline pressure 34 may comprise an average or mean pressure (line 34A), or the baseline pressure 34 may comprise a second range of pressures $R_2$ that is equal to the distance between a highest base pressure (line 34B) and a lowest base pressure (line 34C). In the illustrated example, the highest base pressure 34B is about 9.2 cm $H_2O$, and the lowest base pressure 34C is about 7.6 cm $H_2O$. The median base pressure 34A is about 8.4 cm $H_2O$, and the range $R_2$ (9.2-7.6) is about 1.6 cm $H_2O$. The first and second pressure ranges $R_1$ and $R_2$ are preferably relatively small (e.g. 0.5 cm $H_2O$ or less) to provide relatively constant peak and base pressures 36 and 34, respectively. However, the range $R_1$ and $R_2$ may be larger (e.g. 1.0 cm $H_2O$ or 2.0 cm $H_2O$ or larger). The difference $\Delta P$ between median pressures 34A and 36A is preferably greater than 1.0 cm $H_2O$ or greater than 1.0 cm $H_2O$ and more preferably about 3.0 cm $H_2O$ if device 10 is configured to provide BiPAP-like functionality. $\Delta P$ is preferably greater than 5.0 cm $H_2O$ or greater than 10.0 cm $H_2O$, and more preferably about 15.0 cm $H_2O$ if device 10 is configured to provide NIPPV-like functionality.

Also, in the illustrated example, the peak pressure 36 is maintained for a time $t_1$ of about 0.6 seconds, and the base pressure 34 is maintained for a time $t_2$ of about 1.3 seconds, such that the period P is about 1.9 seconds. Time $t_1$ is preferably about 0.3 to 3.0 seconds, and time $t_2$ is preferably about 0.6 to 6.0 seconds. The period P corresponds to the breathing frequency in cycles per minute. The frequency may be set to meet the requirements of a particular application or needs of a specific patient. Typically, the device 10 is configured (adjusted) to provide a frequency in the range of about 10 to 50 breaths per minute. For example, the device 10 may be configured to provide 15 breaths per minute, 30 breaths per minute, or 45 breaths per minute. The ratio of time $t_2$ at the lower pressure to the time $t_1$, at the higher pressure is preferably about 2.0, but may be less (e.g. 1.0) or larger (e.g. 3.0, 4.0, or greater). Thus, the period P is generally about 1.3 to 2.0 seconds. The transition times $\Delta_1$ and $\Delta_2$ from base pressure 34 to peak pressure 36 and from peak pressure 36 to base pressure 34, respectively, may be small. In the illustrated example transition time's $\Delta_1$ and $\Delta 2$ are about 0.1 seconds or less. However, larger transition times $\Delta_1$ and $\Delta_2$ may also be utilized. It will be understood that the peak pressures 36, 36A, 36B, and 36C, the base pressures 34, 34A, 34B, and 34C may be adjusted as required for a particular application by adjusting the configuration of device 10 of FIGS. 1-4 and 7-8. Similarly, the times $t_1$, $t_2$, $\Delta_1$, $\Delta_2$, and P may also be adjusted as required by adjusting the configuration of device 10 of FIGS. 1-4 and 7-8.

Figure 9:
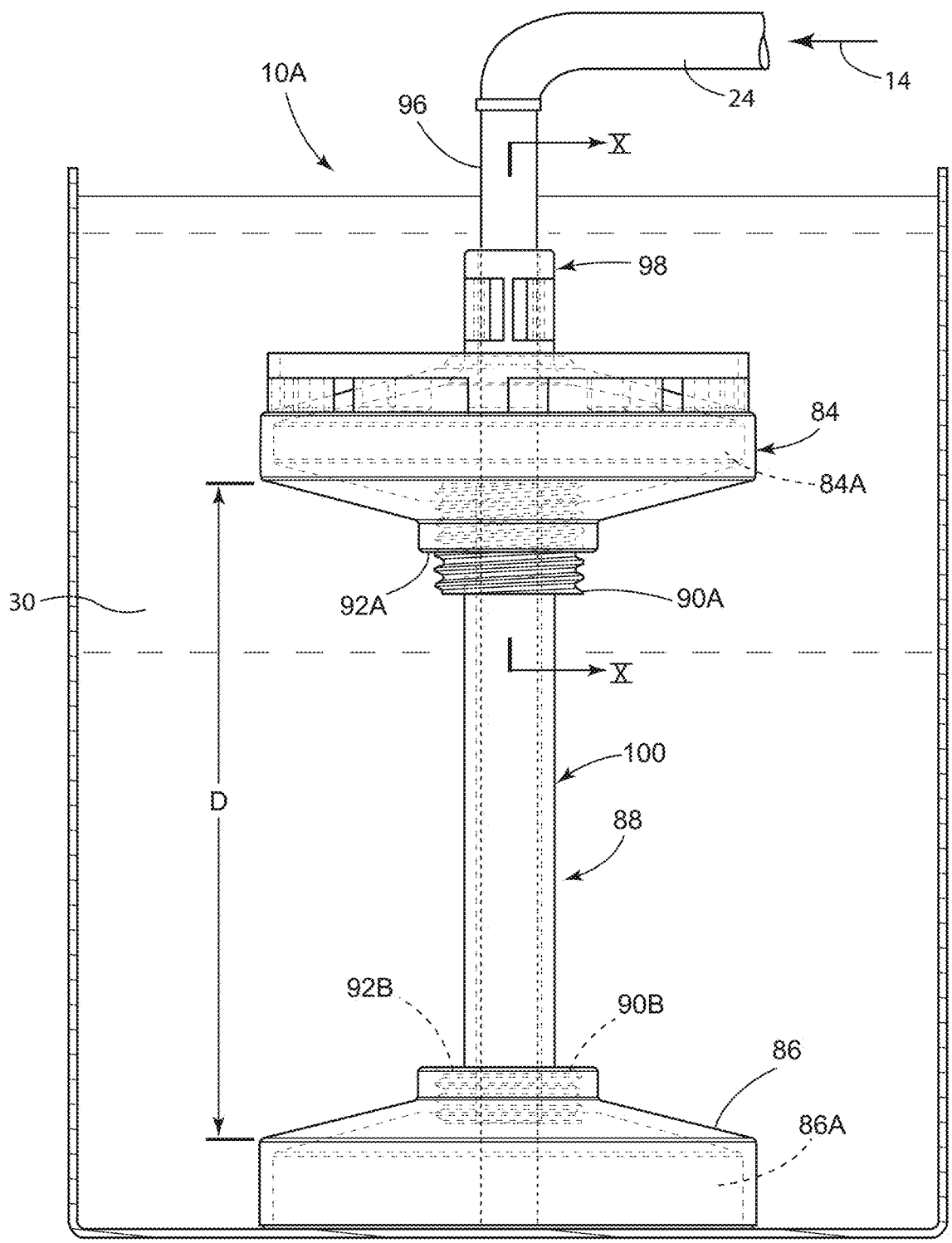
FIG. 9 is a partially fragmentary view of an oscillatory relief valve mechanism according to another aspect of the present invention.
Figure 10:
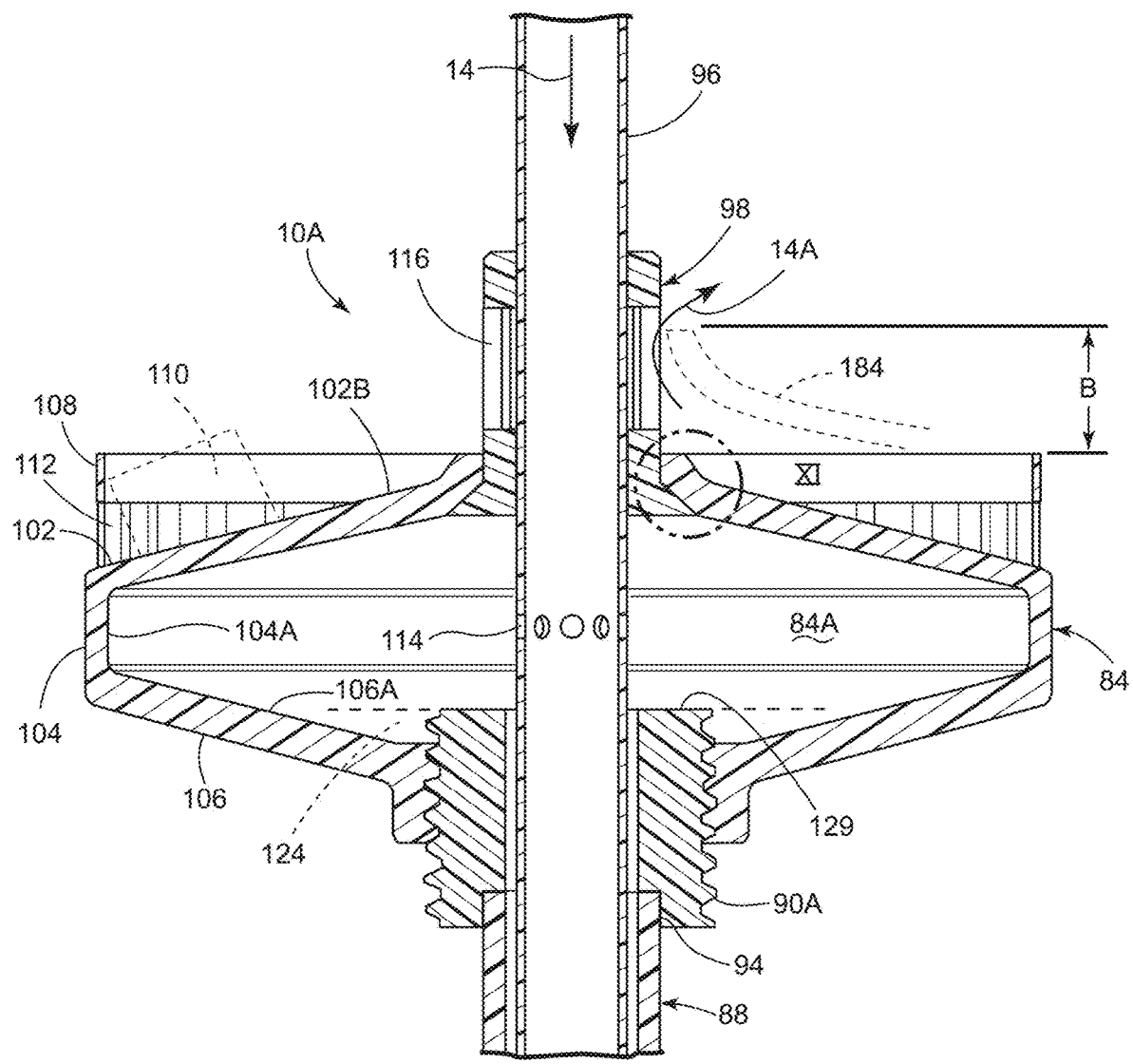
FIG. 10 is a cross sectional view of the mechanism of FIG. 9 taken along the line X-X.
Figure 11:
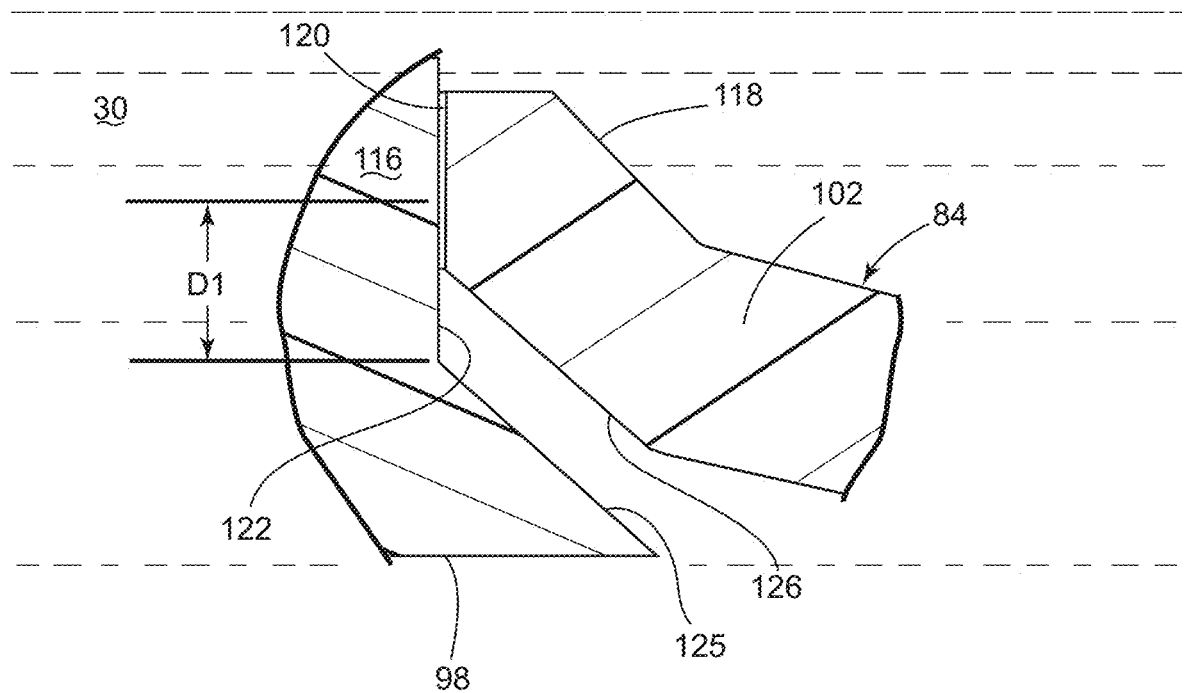
FIG. 11 is an enlarged, fragmentary view of a portion of the device of FIG. 10.

With further reference to FIGS. 9-11, a device 10A according to another aspect of the present invention may be connected to a bubbler branch 24 that supplies gas/air 14 in substantially the same manner as discussed above in connection with FIGS. 1-8. Device 10A includes an upper basket 84, a lower basket 86, and a tube 88 extending between upper and lower baskets 84 and 86. Upper basket 84 includes a hollow interior space 84A, and lower basket 86 includes a hollow interior space 86A. Tube 88 includes a threaded upper portion 90A that is threadably received in a threaded opening 92A of upper basket 84, and a threaded lower portion 90B that is threadably received in a threaded opening 92B of lower basket 86. Threaded portions 90A and 90B may be integrally formed with tube 88, or the threaded portions may be adhered to tube 88 via adhesive at a seam 94 (FIG. 10). The distance "D" between upper basket 84 and lower basket 86 can be adjusted by rotating baskets 84 and 86 relative to tube 88 to move the baskets due to threaded portions 90A, 90B. Tube 88 may also or alternatively include a telescoping feature (not shown) to adjust the length of tube 88. Tubes 88 (not shown) having different lengths may also be interconnected with baskets 84 and 86 to change the distance "D" and adjust the operation of mechanism 10A.

An air supply tube 96 extends vertically through basket 84, tube 88, and through lower basket 86. A vent member 98 may be fixed to the air supply tube 96. The vent member 98 does not move relative to the air supply tube 96. However, the upper basket 84, lower basket 86, and tube 88 together form a moving assembly 100 that slides vertically along air supply tube 96 in a reciprocating manner as discussed in more detail below.

Referring to FIG. 10, upper basket 84 includes an upper sidewall 102, a vertical (cylindrical) sidewall 104, and a lower sidewall 106. Upper sidewall 102 includes an inner surface 102A that is generally conical. Sidewall 104 includes an inner surface 104A that is generally cylindrical, and lower sidewall 106 includes an inner surface 106A that is generally conical. A support or fence structure 108 extends above upper sidewall 102. Optional weights 110 may be positioned on upper sidewall 102 inside support 108 to thereby increase the amount of air (gas 14) that needs to be received in cavity 84A of upper basket 84 (and cavity 46A to move assembly 100 upwardly). Support/fence 108 may include a plurality of openings 112 that permit water to drain off upper surface 102B of upper sidewall 102.

Tube 96 may include one or more openings 114 that permit gas 14 to flow from inside tube 96 into cavity 84A of upper basket 84. Additional gas 14 may flow through tube 96 downwardly into cavity 86A of lower basket 86. When sufficient fluid 30 is displaced from cavities 84A and 86A, the buoyancy causes assembly 100 to shift upwardly, thereby shifting upper basket 84 upwardly a distance "B" to an upper position 184. The gas that was previously trapped in cavity 84A and 86A then flows outwardly through windows 116 of vent member 98 as shown by the arrow 14A (FIG. 10). After a sufficient volume of gas 14A escapes, the moving assembly 100 (i.e. basket 84, tube 88, and basket 86) moves downwardly.

With further reference to FIG. 11, upper sidewall 102 of upper basket 84 includes an angled lip portion 118 having a cylindrical inner surface 120 that slides vertically along cylindrical outer surface 122 of vent member 98. Vent member 98 includes a conical seal surface 125 that engages a corresponding conical seal surface 127 formed on lip 118 of upper sidewall 102 of basket 84. When basket 84 is in a lowered position (FIG. 10), the surfaces 125 and 126 sealingly engage each other such that gas 14 disposed in interior cavity 84 of upper basket 84 cannot escape. However, as discussed above, when upper basket 84 moves upwardly to the upper position 184 (FIG. 10), the conical surfaces 125 and 126 are spaced-apart. This permits the gas to escape through windows 116 as shown by the arrow 14A.

The tapered/conical surfaces 125 and 126 promote self alignment of the upper basket 84 relative to the vent member 98 and tube 96. Also, because the basket 184 must travel a distance "D1" (FIG. 11) before gas 14 can escape through window 116, this permits momentum to build, which carries the moving assembly 100 upwardly to a point where gas 14 evacuates quickly through the windows 116.

Referring again to FIG. 10, the position of upper end 129 of threaded member 90A within cavity 84A can be adjusted by rotating the basket relative to threaded member 90A. Advancing the end 129 of threaded member 90A upwardly into cavity 84A causes the threaded member 90A to trap off a portion 124 of the volume of interior cavity 84A so that the gas 14 cannot be captured in the portion 124 of cavity 84A that is below end 129 of threaded member 90A. The total buoyancy of upper basket 84 and lower basket 86A is determined by the volume of gas 14 disposed in the cavities 84A and 86A. Thus, if the volume of portion 124 is increased, the amount of gas that fills cavity 84A is reduced, and more gas 14 must be pushed into cavity 86A of lower basket 86 before the moving assembly 100 will shift vertically due to the buoyancy of the gas 14 in cavities 84A and 86A. In this way, the volume ratio of the cavities 84A and 86A can be adjusted.

In use, a physician or other user may desire to be able to control cycle time, mean airway pressure (MAP), inspiratory and expiratory pressures, and the ratio of the pressures of the inspiratory and expiratory phases of the waveform (the I:E ratio). The device 10A provides for control of cycle time, waveform, MAP and I:E ratio, and further provides for control of inspiratory and expiratory pressures.

In the device 10A, the internal volume distribution of the device (as a function of depth) can be used for precise control of waveform (e.g. FIG. 5). The device 10A includes two distinct volumes 84A and 86A which capture gas 14, allowing two distinct pressures in the waveform. The ratio of these two distinct volumes can be used to precisely control the time duration of the two pressures, and thus the map and the I:E ratio. It is noted that the I:E ratio is essentially independent of flow rate, and total cycle time can also be controlled independently of the I:E ratio. Cycle time may be adjusted/varied utilizing a controlled leak valve or similar device upstream of device 10A.

In the device 10A, the ratio of the volumes (and the I:E ratio) is controlled by movement of the threaded tube 88. As discussed above, advancing the tube 88 upwards (from the lowest referenced position which has the maximum top basket volume), the tube location traps off a portion 124 of the top volume 84A so that gas 14 cannot be captured in the portion 124. Consequently, in order to be sufficiently buoyant to lift the moving assembly 100, more gas 14 must be pushed into the lower basket 86 through air supply tube 96. The volume ratio between the baskets 84 and 86 is thus changed, as is the I:E ratio and MAP. Other ways to change the volume ratio include providing an expandable top basket 84 having threaded, sliding, etc. portions that can be moved to adjust the volume of space 84A. Leak rate and weights 110 (FIG. 10) can also be used to control cycle time. In device 10A, weights 110 can be positioned inside support/fence 108 without removing device 10A from the water 30, and without pausing operation of device 10A.

Also, as discussed above, the upper and lower walls 102 and 106, respectively, of upper basket 84 are generally conical. The conical inner surfaces 102A and 106A permit escape of gas 14 upwardly and water 30 downwardly, even if device 10A is misaligned from a vertical axis.

The use of two baskets (i.e. upper basket 84 and lower basket 86) creates a waveform in which two distinct (i.e. different) pressures are created. The waveform is well controlled in a substantially square waveform. However, other waveforms are also possible. The more general form has an arbitrary volume distribution as a function of depth. The integral of area over depth (∫Adh) controls the volume displaced as a function of depth (where depth is directly related to pressure). The volume displaced, times the density of the liquid, must exceed the weight (controllable) for the movable assembly 100 to lift, vent, and start a new cycle. Because the volumetric flow rate is relatively constant, each distribution of cross sectional area (as a function of depth) has a corresponding pressure vs time waveform. Thus, the volume distribution between upper basket 84 and lower basket 86 controls the waveform.

The following is a simplified mathematical model describing functioning of the device 10A.

Assume that overall friction and drag are negligible. Assume also that the system is quasi-static and the transitions occur quickly. (This is supported by experimental data.) Defined I/E ratio (φ) as a ratio of time at the different target pressures:

$$\Phi = \frac{t_{insp}}{t_{exp}} \tag{1}$$

The relationship between flow rate and volume may be examined. First, flow is conserved:

$$\dot{V}_{flowthrough} = \dot{V}_{totalflow} - \dot{V}_{leak}$$

As air flows into the device 10A and becomes trapped, eventually a sufficient volume of water is displaced to cause buoyancy of the device. The total volume of air in a cycle is a combination of expiratory, inspiratory, tubing, and leaks volumes given by:

$$V_{exp} = \dot{V}_{flowthrough} t_{exp}$$

$$V_{insp} = \dot{V}_{flowthrough} t_{insp}$$

$$V_{tube} = \dot{V}_{flowthrough} t_{tube}$$

$$V_{leak} = \dot{V}_{leak} t_{cycle}$$

The total trapped air (system) volume can be related to the flow rate through the system (not leaked):

$$V_{sys} = \dot{V}_{flowthrough} t_{cycle}$$

The equations can be solved for time:

$$t_{exp} = \frac{V_{exp}}{\dot{V}_{flowthrough}} \tag{2}$$

$$t_{insp} = \frac{V_{insp}}{\dot{V}_{flowthrough}}$$

$$t_{tube} = \frac{V_{tube}}{\dot{V}_{flowthrough}}$$

$$t_{cycle} = \frac{V_{sys}}{\dot{V}_{flowthrough}}$$

Total time and system volume are sums of flow rates for the different pressures:

$$t_{cycle} = t_{tube} + t_{insp} + t_{exp}$$

$$V_{sys} = V_{tube} + V_{insp} + V_{exp}$$

Substituting the time equations (2) into the I:E ratio equation (1):

$$\Phi = \frac{V_{insp}}{V_{exp}} \tag{3}$$

The above is a significant result; that is, that the I:E ratio is the ratio of the air volumes trapped in the two baskets 84 and 86.

Equilibrium also holds:

$$W - F_{insp} - F_{exp} = 0$$

$$W - g\rho V_{insp} - g\rho V_{exp} = 0$$

Where: W is weight, $F_{insp}$ is the buoyancy contributed by the air trapped at the inspiratory pressure depth, and $F_{exp}$ is the buoyancy contributed by the air trapped at the expiratory depth.

Weight is mass times gravity:

$$gM - g\rho V_{insp} - g\rho V_{exp} = 0$$

This is solved for the volume of the inspiratory depth air:

$$V_{insp} = \frac{M - \rho V_{exp}}{\rho} \tag{4}$$

There are two equations. The equilibrium equation (4) and the derived of I:E ratio (3). Substituting one into the other:

$$\Phi = \frac{M - \rho V_{exp}}{\rho V_{exp}} \tag{5}$$

The above equation (5) can be solved for the expiratory volume, which can be back substituted into inspiratory trapped air volume.

$$V_{exp} = \frac{M}{\rho(1 + \Phi)}$$

$$V_{exp} = \frac{\Phi M}{\rho(1 + \Phi)}$$

Thus, for any given system mass and desired I:E ratio, the target trapped air volumes can be determined.

Control of the cycle time is also possible. This may be done by controlling mass and flow rate. Total cycle time is:

$$t_{cycle} = t_{tube} + t_{insp} + t_{exp}$$

Where $t_{tube}$ is the time required to fill the down tube, $t_{insp}$ is the time to fill the inspiratory trapped air volume, and $t_{exp}$ is the time to fill the expiratory trapped air volume.

The times during any given phase are:

$$t_{exp} = \frac{V_{exp}}{\dot{V}_{flowthrough}}$$

-continued $$t_{insp} = \frac{V_{insp}}{\dot{V}_{flowthrough}}$$

$$t_{tube} = \frac{V_{tube}}{\dot{V}_{flowthrough}}$$

Thus:

$$t_{cycle} = \frac{V_{insp}}{\dot{V}_{flowthrough}} + \frac{V_{exp}}{\dot{V}_{flowthrough}} + \frac{h\pi r^2}{\dot{V}_{flowthrough}}$$

In the above equation, r is the radius of the down tube 96 carrying air from top basket 84 to bottom basket 86, and h is the length of the down tube 96.

Substituting volumes:

$$t_{cycle} = \frac{M}{\dot{V}_{flowthrough}\, \rho(1+\Phi)} + \frac{\Phi M}{\dot{V}_{flowthrough}\, \rho(1+\Phi)} + \frac{h\pi r^2}{\dot{V}_{flowthrough}}.$$

Therefore the total cycle time is:

$$t_{cycle} = \frac{M + h\pi r^2 \rho}{\dot{V}_{flowthrough}\, \rho}$$

Thus, we have three summative equations.

$$V_{exp} = \frac{M}{\rho(1+\Phi)} \quad (6)$$

$$V_{insp} = \frac{\Phi M}{\rho(1+\Phi)}$$

$$t_{cycle} = \frac{M + h\pi r^2 \rho}{\dot{V}_{flowthrough}\, \rho}$$

Recall that the primary concerns are typically I:E, h, and cycle time (the inputs) and it may be important to determine is $V_{exp}$ and mass (M). It is noted that inspiratory volume is typically not critical for sizing. A large inspiratory basket that is open ended at the bottom may be utilized. The inspiratory trapped air volume will be automatically established within this bottom basket (because of the equilibrium relationship between total displaced volume and mass).

It is also noted that in the above equations (6), the "flow through volume"($V_{flowthrough}$) and its time derivative "flow through rate" ($\dot{V}_{flowthrough}$) refers to the volume that goes through the system in a cycle (exclusive of leaks), not the volume which is available for the patient. As the system can be downstream of the patient, a portion of the patient volume can be leaked intentionally to control the cycle time. Thus, a dimensionless leak rate ($\gamma$) can be defined:

$$\gamma = \frac{\dot{V}_{leak}}{\dot{V}_{totalflow}}$$

$$\dot{V}_{flowthrough} = \dot{V}_{totalflow}(1-\gamma)$$

The third equation thus becomes:

$$t_{cycle} = \frac{M + h\pi r^2 \rho}{\dot{V}_{totalflow}\, \rho(1-\gamma)}$$

For the system designer/user, the three equations can be solved to obtain desirable device values:

$$V_{exp} = \frac{\dot{V}_{totalflow}\, t_{cycle}(1-\gamma) - h\pi r^2}{1+\Phi}$$

$$M = \rho\left(\dot{V}_{totalflow}\, t_{cycle}(1-\gamma) - h\pi r^2\right)$$

$$V_{insp} = \frac{\Phi\left(\dot{V}_{totalflow}\, t_{cycle}(1-\gamma) - h\pi r^2\right)}{1+\Phi}$$

Note that $V_{insp}$ is the lower limit size of the open ended bottom basket 86. The other values set the required size of top basket 84 (which is adjustable as described previously) and the mass (ballast 110 can be added).

The above analysis is simplified, and ignores friction and dynamics. However, it provides guidance to a user of the system 10A the device 10A to provide the desired outcome. As a basic validation, a physical sizing calculation can be done. Assume some clinically relevant values:

$$\dot{V}_{totalflow} = \frac{3 \text{ liters}}{\text{min}}$$

$$\Phi = 0.5$$

$$t_{cycle} = 2 \text{ secs}$$

$$h = 15 \text{ cm}$$

$$\gamma = 0.1$$

$$r = 0.5 \text{ cm}.$$

In the above assumptions, r is the ratio of the source air tube which does not contribute to buoyancy under the assumption that the source air tube continues downward to the bottom basket. This source air tube is used for alignment, and is restrained in the exemplar embodiment.

These calculated assumptions lead to calculated sizes of:

$V_{exp}$=52.15 cm$^3$ $M$=78.22 grams $V_{insp}$=26.07 cm$^3$

These volumes and the mass are consistent and within reasonable margins of error with a prototype device and laboratory data.

If a device 104 has already been set up, the three equations can also be solved for expected performance.

$$\Phi = \frac{M - \rho V_{exp}}{\rho V_{exp}}$$

$$t_{cycle} = \frac{M + h\pi r^2 \rho}{\dot{V}_{totalflow}\, \rho(1-\gamma)}$$

$$V_{insp} = \frac{M - \rho V_{exp}}{\rho}$$

Figure 12:
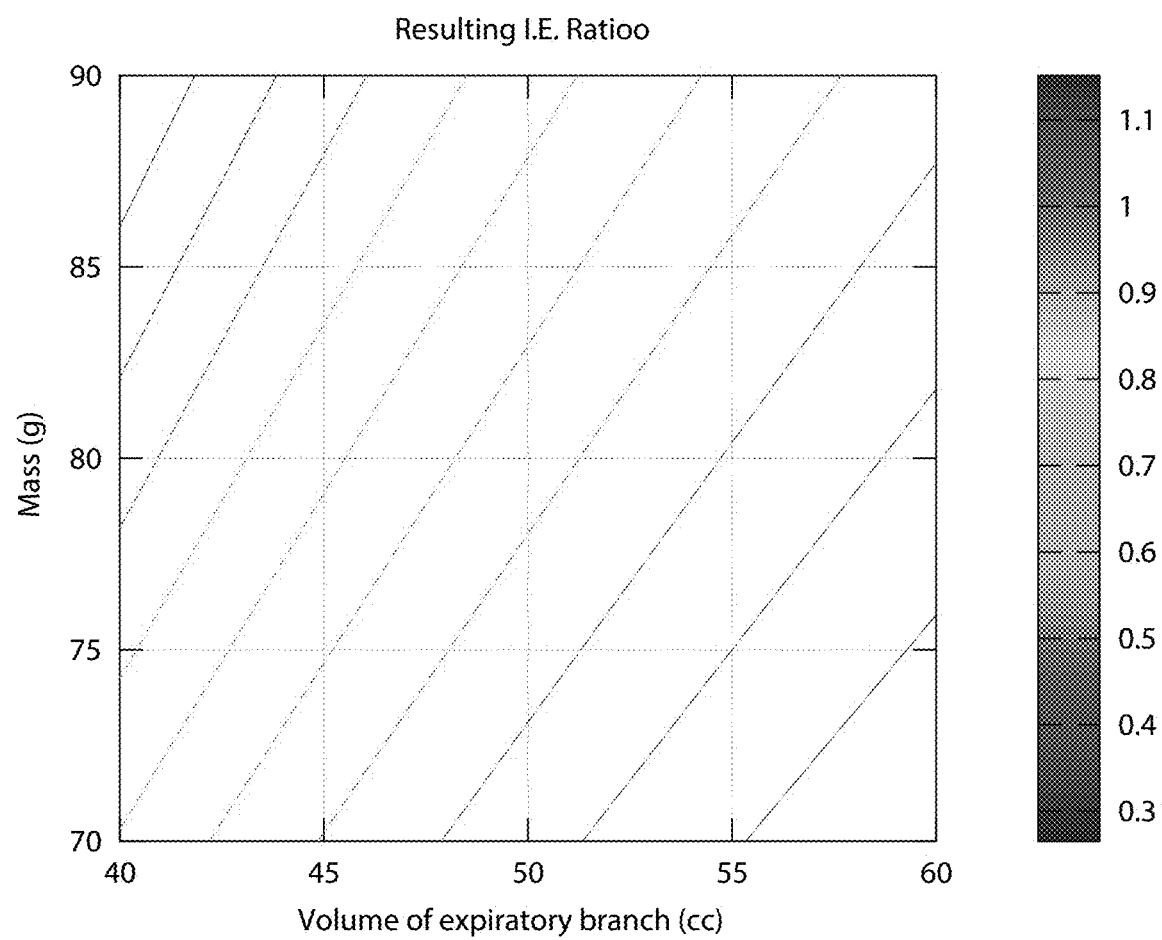
FIG. 12 is an example of a performance chart for the mechanism of FIGS. 8-10.
Figure 13:
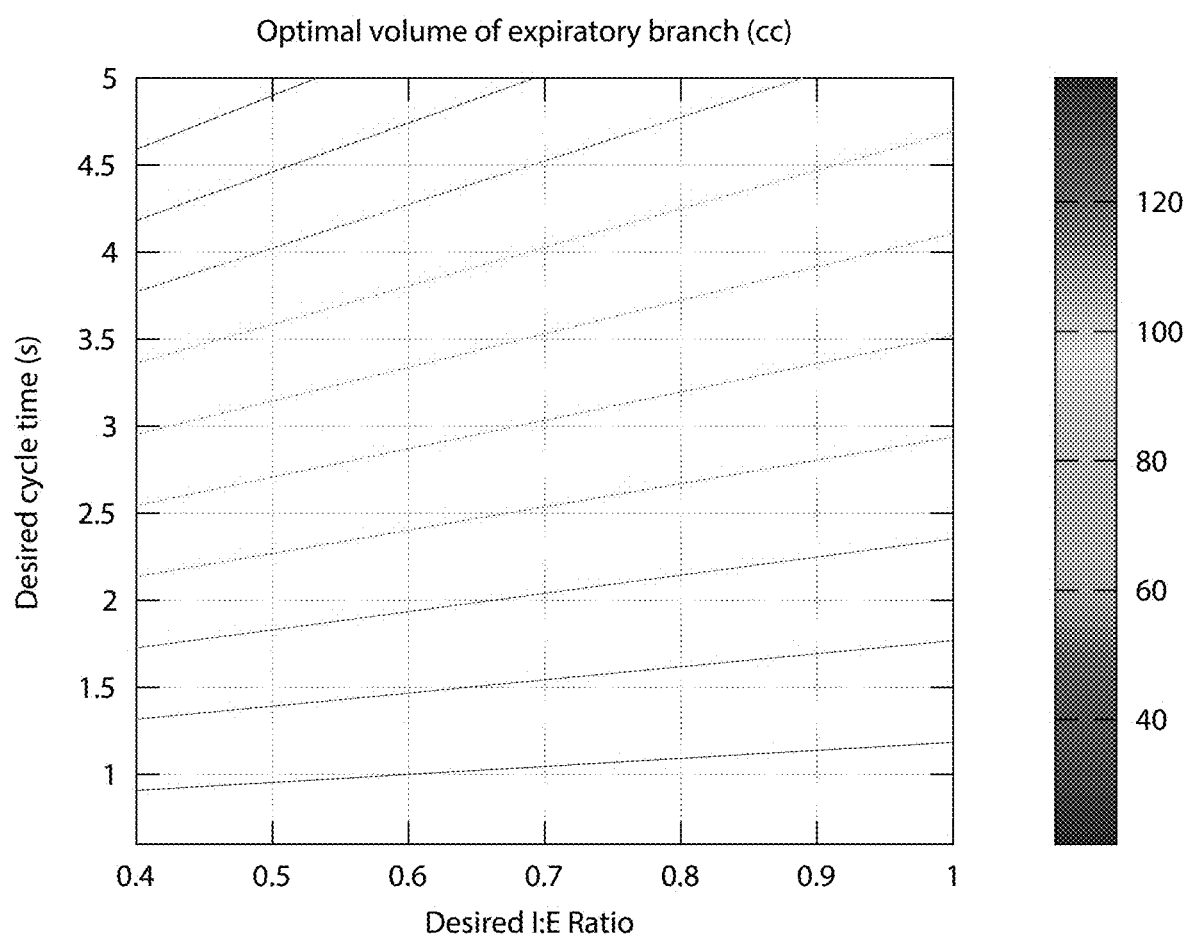
FIG. 13 is an example of a performance chart for the mechanism of FIGS. 8-10.
Figure 14:
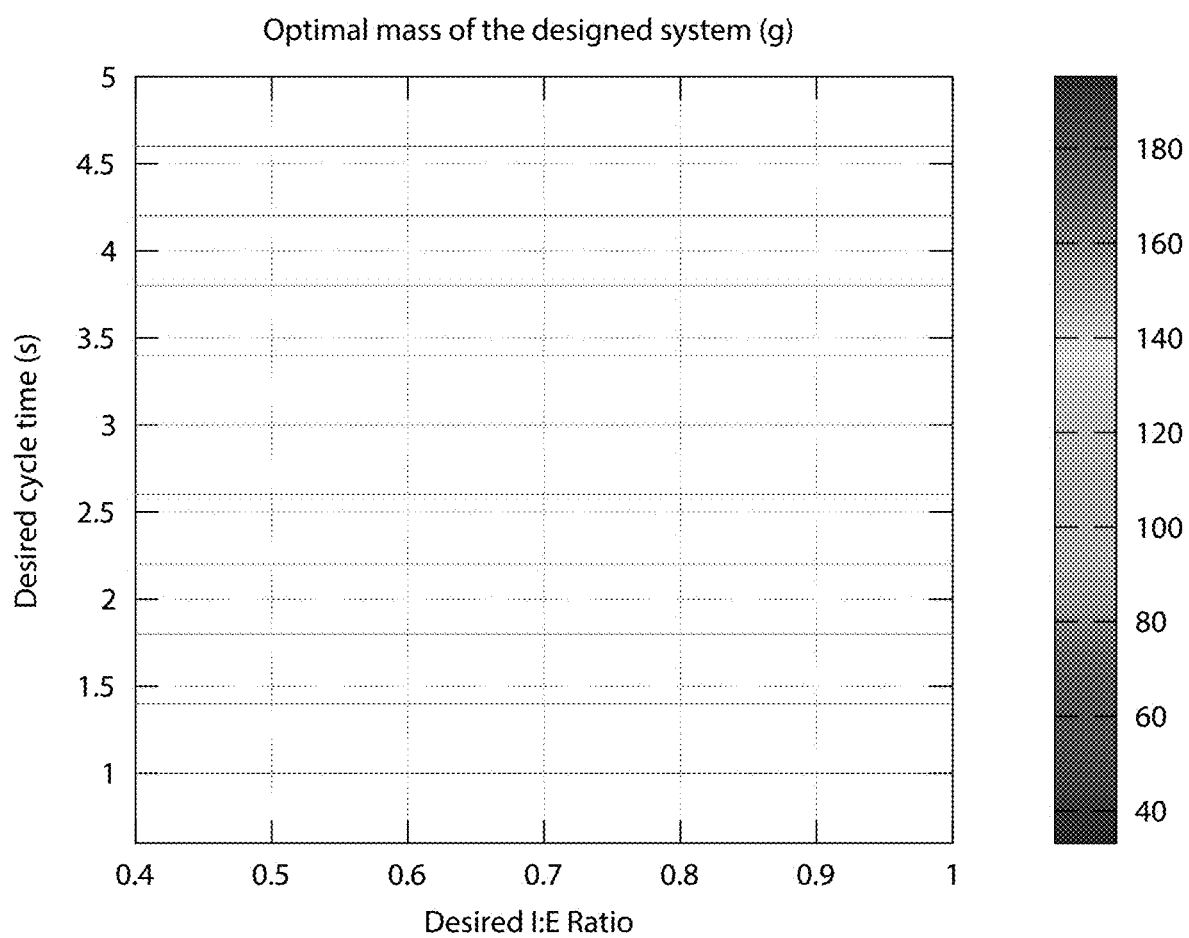
FIG. 14 is an example of a performance chart for the mechanism of FIGS. 8-10.

The derived equations can be used to set up a graphical performance charts (FIGS. 12-14). These charts provide a reference for the designer/user which allows them to determine device settings based on certain performance characteristics.

Thus, the ability to control volume ratios in device 10A provides control of the I:E and MAP.

It is also noted that the construction and arrangement of the elements of the devices as shown and described in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited.

For example, first tube 28 is configured to provide a vertical slide/guide and to provide gas that is received in basket 42 to provide oscillating movement of basket 42. However, a separate guide structure such as a vertical rod or the like (not shown) may be utilized to guide basket 42, and tube 28 does not necessarily act as a guide. Elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength, durability, or density in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above is merely for illustrative purposes and not intended to limit the scope of the device, which is defined by the following claims as interpreted according to the principles of patent law, including the Doctrine of Equivalents.

What is claimed is:

1. A dual pressure respiratory assistance device, comprising:
    a gas source which supplies a flow of gas into an air tube, wherein the air tube has a patient branch and a bubbler branch that are fluidly interconnected;
    a first tube fluidly connected to the bubbler branch, wherein the first tube is at least partially submerged in a fluid; and
    an oscillatory relief assembly including an oscillating member that is configured to capture gas released through at least one hole in the first tube when the oscillating member is in a first position, and wherein a collection of gas in the oscillating member causes the oscillating member to rise through the fluid to a second position, and wherein the gas is released from the oscillating member when the oscillating member reaches the second position, whereby the oscillatory relief assembly causes pressure in the patient branch to cycle between at least a first pressure range and a second pressure range.

2. The dual pressure respiratory assistance device of claim 1, wherein:
    the oscillatory relief assembly causes the pressure in the patient branch to remain at the first and second pressures for first and second periods of time, respectively.

3. The dual pressure respiratory assistance device of claim 2, wherein:
    the oscillatory relief assembly transitions from the first pressure to the second pressure in a period of time that is significantly less than the first and second periods of time.

4. The dual pressure respiratory assistance device of claim 3, wherein:
    the first pressure range is about 10 cm $H_2O$ or less.

5. The dual pressure respiratory assistance device of claim 4, wherein:
    the second pressure range is about 20 cm $H_2O$ or less.

6. The dual pressure respiratory assistance device of claim 3, wherein:
    the first and second pressures comprise first and second median pressures, respectively, and wherein a difference between the first and second median pressures is at least 1.0 cm $H_2O$.

7. The dual pressure respiratory assistance device of claim 6, wherein:
    the difference between the first and second median pressures is about 3.0 cm $H_2O$.

8. The dual pressure respiratory assistance device of claim 6, wherein:
    the difference between the first and second median pressures is about 15.0 cm $H_2O$.

9. The dual pressure respiratory assistance device of claim 2, wherein:
    the first period of time is about 0.3 to about 3.0 seconds, and the second period of time is about 0.6 to about 6.0 seconds.

10. The dual pressure respiratory assistance device of claim 9, wherein:
    the pressure in the patient branch oscillates at about 10-50 cycles per minute.

11. The dual pressure respiratory assistance device of claim 1, wherein:
    the pressure in the patient branch oscillates in a periodic manner to define a frequency.

12. The dual pressure respiratory assistance device of claim 1, wherein:
    the gas source supplies the flow of gas at a constant pressure.

13. The dual pressure respiratory assistance device of claim 1 wherein:
    the oscillating member is slidably connected to the first tube.

14. The dual pressure respiratory assistance device of claim 13, wherein:
   the first tube includes a vertically-extending portion;
   the oscillating member is slidably connected to the vertically-extending portion.

15. The dual pressure respiratory assistance device of claim 14, wherein:
   the oscillatory relief assembly includes a shell disposed on the first tube, wherein the shell includes at least one passageway through a sidewall of the shell whereby gas is released through the passageway when the oscillating member reaches the second position.

16. The dual pressure respiratory assistance device of claim 15, wherein:
   the oscillating member includes an interior space having a partial or complete enclosure disposed above or around the at least one hole in the first tube whereby gas that is released through the at least one hole in the first tube travels upwardly through the fluid into the interior space of the oscillating member.

17. The dual pressure respiratory assistance device of claim 16, wherein:
   the oscillating member comprises an upper basket having an interior cavity, a lower basket having an interior cavity, and a tube extending between and interconnecting the upper and lower baskets;
   gas from the gas source flows through the first tube in a downstream direction;
   the at least one hole in the first tube comprises at least one upstream hole that opens to the interior cavity of the upper basket when the oscillating member is in the first position;
   the first tube including at least one downstream hole that is downstream of the at least one upstream hole, and wherein gas released from the at least one downstream hole enters the interior cavity of the lower basket.

18. The dual pressure respiratory assistance device of claim 17, wherein:
   the interior cavity of the upper basket defines a first volume;
   the interior cavity of the lower basket defines a second volume; and
   at least one of the first and second volumes is adjustable to adjust at least one of mean airway pressure (MAP) and a ratio of the pressure of inspiratory and expiratory phases of a pressure in the patient branch.

19. A kit for converting a bubble-CPAP machine to a dual pressure respiratory assistance device, the kit comprising:
   a shell having a side wall and having a first conical seal surface and at least one passageway through the side wall above the first conical seal surface, wherein the shell is sized to fit around a first tube which is at least partially submerged in a fluid; and
   an oscillating member comprises an upper basket having an interior cavity, a lower basket having an interior cavity, and a tube extending between and interconnecting the upper and lower baskets, the upper basket having a top portion which fits closely around the side wall of the shell and is able to slide with respect to the shell, and a second conical seal surface configured to engage the first conical seal surface when the oscillating member is in a first position, wherein the upper wall is adapted to capture gas bubbles in the interior cavity of the upper basket when the oscillating member is in the first position and thereby increase the buoyancy of the oscillating member whereby the oscillating member moves to a second position in which the first and second seal surfaces are spaced apart to form a gap such that air from inside the interior cavity of the upper basket flows through the gap and through the passageway of the shell to thereby reduce the buoyancy of the oscillating member.

20. A method of providing respiratory assistance to a patient, comprising the steps of:
   initiating a gas flow into a passageway, wherein the passageway branches into a bubbler branch and a patient branch;
   at least partially submerging a portion of the bubbler branch of the passageway with an oscillatory relief valve disposed thereon in a container of fluid;
   positioning a patient air supply interface on the patient, wherein the patient air supply interface is fluidly connected to the patient branch;
   causing the oscillatory relief valve to capture gas escaping from the bubbler branch when the oscillatory relief valve is at a first position to thereby cause the oscillatory relief valve to move upwardly from the first position to a second position;
   causing gas to be released from the oscillatory relief valve when the oscillatory relief valve is at the second position to thereby cause the oscillatory relief valve to move downwardly from the second position to the first position; and
   wherein movement of the oscillatory relief valve between the first and second positions causes gas pressure within the patient branch to oscillate between first and second magnitudes.

\* \* \* \* \*